United States Patent [19]

Ryan

[11] 4,191,753
[45] Mar. 4, 1980

[54] ANTI-HYPERTENSIVE PEPTIDE ANALOGS

[75] Inventor: James W. Ryan, Miami, Fla.

[73] Assignee: University of Miami, Miami, Fla.

[21] Appl. No.: 958,179

[22] Filed: Nov. 6, 1978

[51] Int. Cl.$^2$ .................... A61K 37/00; C07C 103/52
[52] U.S. Cl. ............................. 424/177; 260/112.5 R
[58] Field of Search .................. 424/177; 260/112.5 R

[56] References Cited
PUBLICATIONS

Ferreira et al., Biochemistry 9, 1970, 2583-2593.

Ondetti et al., Biochemistry 19, 1971, 4033-4039.

*Primary Examiner*—Delbert R. Phillips

[57] ABSTRACT

Novel peptides having the sequence

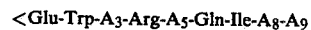

wherein $A_3$, $A_5$, $A_8$ and $A_9$ are either L-proline or L-3,4-dehydroproline, are disclosed. These peptides are potent inhibitors of angiotensin converting enzyme and are useful as antihypertensive agents.

15 Claims, No Drawings

ANTI-HYPERTENSIVE PEPTIDE ANALOGS

BACKGROUND OF THE INVENTION

Angiotensin converting enzyme (peptidyldipeptide hydrolase, hereinafter referred to as ACE) occupies a central role in the physiology of hypertension. The enzyme is capable of converting the decapeptide angiotensin I, having the sequence AspArgValTyrIleHisProPheHisLeu to an octapeptide, angiotensin II by removal of the carboxyterminal HisLeu. The symbols for various chemical entities are explained in the following table:

Ala=L-alanine
Arg=L-arginine
Asp=L-aspartic acid
<Glu=pyro-L-glutamic acid
Gly=glycine
Hip=Hippuric acid (Benzoyl glycine)
His=L-histidine
Ile=L-isoleucine
Leu=L-leucine
Phe=L-phenylalanine
Pro=L-proline
ΔPro=L-3,4-dehydroproline
Ser=L-serine
Trp=L-tryptophan
Tyr=L-tyrosine
Val=L-valine
ACE=Angiotensin converting enzyme
Hepes=N-2-hydroxyethylpiperazine-N'-2-ethanesulfonic acid Angiotensin I is formed by the action of the enzyme renin, an endopeptidase found in kidney, other tissues and plasma, acting on a serum α-2 globulin.

Blood pressure is affected by certain peptides found in the blood. One of these, angiotensin II, is a powerful pressor (blood pressure elevating) agent. Another, bradykinin, a nonapeptide with the sequence ArgProProGlyPheSerProPheArg is a powerful depressor (blood pressure lowering) agent. In addition to a direct pressor effect, angiotensin II stimulates release of aldosterone which tends to elevate blood pressure by causing retention of extracellular salt and fluids. Angiotensin II is found in measurable amount in the blood of normal humans. However, it is found at elevated concentrations in the blood of patients with renal hypertension.

The level of ACE activity is ordinarily in excess, in both normal and hypertensive humans, of the amount needed to maintain observed levels of angiotensin II. However, it has been found that significant blood pressure lowering is achieved in hypertensive patients by treatment with ACE inhibitors. [Gavras, I., and Vukovich, R. A., *New Engl. J. Med.* 291, 817 (1974)].

ACE is a peptidyldipeptide hydrolase. It catalyzes the hydrolysis of the penultimate peptide bond at the C-terminal end of a variety of acylated tripeptides and larger polypeptides having an unblocked α-carboxyl group. The action of ACE results in hydrolytic cleavage of the penultimate peptide bond from the carboxylterminal end yielding as reaction products a dipeptide and a remnant.

The reactivity of the enzyme varies markedly depending on the substrate. At least one type of peptide bond, having the nitrogen supplied by proline, is not hydrolyzed at all. The apparent Michaelis constant (Km) varies from substrate to substrate over several orders of magnitude. For general discussion of the kinetic parameters of enzyme catalyzed reactions, see Lehninger, A., *Biochemistry*, Worth Publishers, Inc., New York, 1970, pp. 153–157. Many peptides which are called inhibitors of the enzymatic conversion of angiotensin I to angiotensin II are in fact substrates having a lower Km than angiotensin I. Such peptides are more properly termed competitive substrates. Bradykinin is an example of a competitive substrate. In addition, a series of peptides isolated from the venom of *Bothrops jararaca*, a South American pit viper have been isolated, see Ferreira, S. H., et al., *Biochemistry* 9, 2583 (1970), which are strong competitive substrates of ACE.

The role of ACE in the pathogenesis of hypertension has stimulated interest in the venom peptides as possible antihypertensive drugs. The most potent is designated $BPP_{9a}$ (for Bradykinin Potentiating Peptide), and also termed SQ 20,881 by Ondetti, M. A., et al., *Biochemistry* 10, 4033 (1971), who have determined its sequence and have synthesized the peptide. The amino acid sequence of $BPP_{9a}$ is <Glu-Trp-Pro-Arg-Pro-Gln-Ile-Pro-Pro. By convention, amino acid sequences are written and numbered left to right, from the N-terminal residue to the C-terminal residue. Substitutions are designated by position number. For example, $\Delta Pro^3\text{-}BPP_{9a}$ has the sequence of $BPP_{9a}$ except the L-3,4-dehydroproline is substituted for the proline at position three. Quantitatively, the inhibitory potency is expressed as the $I_{50}$ value, defined as the concentration of inhibitor required to produce 50% inhibition of the enzyme in a standard assay system containing an approximately Km level of substrate. The $I_{50}$ value for $BPP_{9a}$ is approximately 28 nM. For comparison, $I_{50}$ for bradykinin is approximately 500 nM and $I_{50}$ for D-2-methyl-3-mercaptopropanoyl-L-proline (SQ 14,225, "captopril"), an orally effective antihypertensive compound, is approximately 23 nM.

Gavras, I., et al., *New Engl. J. Med.* 291, 817 (1974) and *Clin. Sci. Mol. Med.* 48, 575 (1975), have shown that $BPP_{9a}$, injected intravenously at 1–4 mg/kg body weight, acts as a potent antihypertensive agent in patients with renin-related hypertension. The drug is also effective in lowering blood pressure of patients with essential hypertension when $BPP_{9a}$ administration follows treatment with moderate doses of diuretics. It is still not certain whether the blood pressure lowering effect of $BPP_{9a}$ is due to the prevention of the conversion of angiotensin I to the potent vasoconstrictor angiotensin II or to the prevention of the destruction of bradykinin by ACE.

In addition, many patients with essential hypertension respond favorably to treatment with $BPP_{9a}$, see Case, D. B., et al., *Am. J. Med.* 61, 790 (1976) and Case, D. B., et al., *New Engl. J. Med.* 296, 641 (1977).

A major research and clinical testing effort has been focussed on the inhibitor SQ 14,225, since it is effective orally. However, in preliminary clinical trials, side reactions have occurred in a number of patients, although their cause is not known. The type of side reactions observed with SQ 14,225 have not been encountered previously with the clinical use of $BPP_{9a}$. In view of the adverse reactions to SQ 14,225 experienced by some patients, and also because of instability of the drug in solution due to disulfide dimer formation, reversion to the clinical use of BPP$_{9a}$ as an antihypertensive agent may be warranted. Reversion to the clinical use of BPP$_{9a}$ will be particularly important for as many as 11% of the patients known to benefit from inhibitors of ACE, but who also respond adversely to SQ 14,225.

At present, little is known about what happens to BPP$_{9a}$ in vivo. A research program has been initiated to gain a better understanding of the metabolic fate and modes of elimination of BPP$_{9a}$. In order to provide tritium-labeled BPP$_{9a}$, novel analogs were synthesized that would be catalytically hydrogenated with tritium gas to yield [$^3$H]-BPP$_{9a}$. Unexpectedly, the analogs proved to be highly potent ACE inhibitors in their own right, some of them being up to 20 times more potent than BPP$_{9a}$ itself.

A wide variety of peptide analogs of BPP$_{9a}$ has been synthesized. See Ondetti, et al., U.S. Pat. No. 3,832,337, issued Aug. 27, 1974; Cushman, D. W., et al., *Experientia* 29, 1032 (1973) and Pluscec, I., et al., *Peptides* 1972, Proc. 12th Europ. Peptide Symp. (H. Hanson and H. D. Jakubke, eds.) North Holland Publ. Co., Amsterdam, 1972, p. 403. From these studies it appears that analogs of similar inhibitory potency can be provided by substituting a cyclopentylcarbonyl for the pyroglutamyl residue, phenylalanine for the tryptophan residue, glycine or histidine for the arginine residue and phenylalanine for the isoleucine residue.

Other substitutions, single and in combination, have been investigated, as disclosed in U.S. Pat. No. 3,832,337. Modest increases in potency have been observed, and a partial pattern of permissible substitutions has been developed. However, few substitutions of proline analogs for any of the proline residues have been tested. In one instance, substitution of a pyrrolidinyl reside at Pro$^9$ resulted in a substantial loss of inhibitory potency. Substitution of an alanine residue at Pro$^8$ somewhat improved inhibitory potency, by a factor of 2.75. (See Cushman, D. W., et al., supra). However, these workers concluded generally that at least the C-terminal pentapeptide sequence -Pro-Gln-Ile-Pro-Pro is required for significant inhibition.

Derivatives of bradykinin having a proline in the 2, 3 or 7 position substituted by L-3,4-dehydroproline have been studied for physiological effect on the contractile response of rat uterus and guinea pig ileum. See Fisher, G. H., et al., *Arch. Biochem. Biophys.* 189, 81 (1978). The analogs $\Delta$pro$^2$-bradykinin and $\Delta$pro$^3$-bradykinin were approximately as effective as bradykinin, while $\Delta$pro$^7$-bradykinin was only about 25% as effective.

SUMMARY OF THE INVENTION

In the course of synthesizing tritiated BPP$_{9a}$, it was unexpectedly observed that certain precursor analogs, intended for catalytic tritiation, containing L-3,4-dehydroproline ($\Delta$Pro) substituted for a proline residue, were substantially more potent as inhibitors of ACE than BPP$_{9a}$ itself. Two of these analogs, $\Delta$Pro$^3$-BPP$_{9a}$ and $\Delta$Pro$^5$-BPP$_{9a}$, are approximately 20 times more potent than BPP$_{9a}$. Another, $\Delta$Pro$^9$-BPP$_{9a}$, is more than 100 times more potent than BPP$_{9a}$. The analog $\Delta$Pro$^8$-BPP$_{9a}$ is also an effective inhibitor of ACE, although somewhat less potent than BPP$_{9a}$. Analogs of BPP$_{9a}$ having L-3,4-dehydroproline substituted for one or more of the proline residues are useful as inhibitors of ACE and as drugs for the treatment of renovascular hypertension.

DETAILED DESCRIPTION OF THE INVENTION

Novel analogs of BPP$_{9a}$, having a proline residue replaced by L-3,4-dehydroproline ($\Delta$Pro) are potent inhibitors of human ACE. In particular, $\Delta$Pro$^3$-BPP$_{9a}$, $\Delta$Pro$^5$-BPP$_{9a}$ and $\Delta$Pro$^9$-BPP$_{9a}$ are more inhibitory than BPP$_{9a}$ itself. The peptides $\Delta$Pro$^3$-BPP$_{9a}$ and $\Delta$Pro$^5$-BPP$_{9a}$ are effective in reducing the mean arterial blood pressure of guinea pigs when administered intravenously at a dose level of 3–4 mg/kg body weight.

Further increases in potency may be expected by inserting $\Delta$Pro in two or more positions of BPP$_{9a}$, including, for example, $\Delta$Pro$^{3,5}$-BPP$_{9a}$, $\Delta$Pro$^{3,9}$-BPP$_{9a}$, $\Delta$Pro$^{5,9}$-BPP$_{9a}$, or $\Delta$Pro$^{3,5,9}$-BPP$_{9a}$. Insertion of $\Delta$Pro at position eight, while not increasing inhibitor potency, may confer resistance to degradation in vivo, and may act synergistically when combined with other substitutions. In addition, increases in potency or improvements in pharmacodynamic properties may be obtained when insertion of $\Delta$Pro is combined with other amino acid substitutions reported in the prior art. An attractive possibility in this regard is the substitution of a cyclopentylcarbonyl (cpc) residue for the pyroglutamyl (<Glu) residue of BPP$_{9a}$. Peptides such as cpc$^1\Delta$Pro$^{3,9}$-BPP$_{9a}$ are expected to exhibit desirable properties as ACE inhibitors and as antihypertensive drugs.

Advantages of the compounds of the present invention are of two types. Their extremely high potency makes it possible to administer lower doses in the treatment of hypertension, reducing the likelihood of side effects and reducing the cost of treatment. Secondly, inclusion of the non-naturally occurring $\Delta$Pro residue may enhance the stability of the peptides in vivo, so that the therapeutic effects are more stable and longer lasting.

The explanation for the greatly increased inhibitory potency of $\Delta$Pro$^3$-BPP$_{9a}$, $\Delta$Pro$^5$-BPP$_{9a}$ and $\Delta$Pro$^9$-BPP$_{9a}$ is not known. The peptides may exert their ACE inhibitory properties by complexing or binding to the enzyme before it can hydrolyze the substrate. The high inhibiting potencies of the $\Delta$Pro$^3$-BPP$_{9a}$ and $\Delta$Pro$^5$-BPP$_{9a}$ analogs might be due to a preferential $\pi$-$\pi$ interaction of the deformed electron cloud of the $\Delta$Pro residue in positions 3 and 5 with binding sites on the enzyme, whereas such an interaction is much less favorable when $\Delta$Pro is located at position eight of the peptide sequence. These data seem to support the hypothesis that introduction of unsaturation into a binding element of a peptide can enhance its affinity for some of its receptors. Such an explanation has been used to account for the greater uterotonic activity of $\Delta$Pro$^7$-oxytocin compared to oxytocin itself, see Moore, S., et al., *J. Med. Chem.* 20, 495 (1977). However, in view of the drastically different effects of $\Delta$Pro substitution at positions eight and nine, the foregoing hypothesis is incomplete. Indeed it may be supported that a variety of mechanisms are brought into play, depending upon the substitution site.

EXAMPLE 1

Synthesis of $\Delta$Pro-substituted BPP$_{9a}$ analogs. All peptides were synthesized by the Merrifield solid-phase technique, as described by Merrifield, R.B., *J. Am. Chem. Soc.* 85, 2149 (1963); Merrifield, R.B., *Biochemistry* 3, 1385 (1964) and Stewart, J.M. and Young, J., *Solid Phase Peptide Synthesis,* W. H. Freeman Co., San Francisco, Calif. (1969). L-3,4-dehydroproline, prepared as described by Felix, A.M., et al., *Int. J. Pept. Prot. Res.* 5, 201 (1973), was provided by Dr. Arthur M. Felix. The peptide products were purified by combinations of gel filtration and partition chromatography columns. The synthetic peptides were homogeneous, as judged by thin layer chromatography in four solvent systems, high performance liquid chromatography and electrophoresis at pH 2 and at pH 5. Amino acid analysis yielded in each case the proper amino acids in the theoretical molar ratios, within experimental error. Peptides synthesized were:

$\Delta$Pro$^3$-BPP$_{9a}$: <Glu-Trp-$\Delta$Pro-Arg-Pro-Gln-Ile-Pro-Pro $\Delta$Pro$^5$-BPP$_{9a}$: <Glu-Trp-Pro-Arg-$\Delta$Pro-Gln-Ile-Pro-Pro $\Delta$Pro$^8$-BPP$_{9a}$: <Glu-Trp-Pro-Arg-Pro-Gln-Ile-$\Delta$Pro-Pro $\Delta$Pro$^9$-BPP$_{9a}$: <Glu-Trp-Pro-Arg-Pro-Gln-Ile-Pro-$\Delta$Pro.

EXAMPLE 2

$\Delta$Pro$^3$-BPP$_{9a}$, $\Delta$Pro$^5$-BPP$_{9a}$, $\Delta$Pro$^8$-BPP$_{9a}$, and $\Delta$Pro$^9$-BPP$_{9a}$ were each compared with BPP$_{9a}$ (<Glu-Trp-Pro-Arg-Pro-Gln-Ile-Pro-Pro; also known as SQ 20,881) for their abilities to inhibit the hydrolysis of [$^3$H]benzoyl-Gly-His-Leu by human urinary angiotensin converting enzyme, prepared as described by Ryan, J., et al., *Tissue and Cell* 10, 555 (1978). A standard amount of enzyme (the amount required to hydrolyze 8% of substrate during the course of incubation at 37° C. for 15 min.) was incubated with [$^3$H]benzoyl-His-Leu in a final reaction volume of 100 $\mu$l or 110 $\mu$l. The reaction mixture contained 0.05 M Hepes buffer, pH 8.0, 0.1 M NaCl, 0.75 M Na$_2$SO$_4$, [$^3$H]-benzoyl-Gly-His-Leu (100 $\mu$M at 10 mCi/mmole, enzyme and varying concentrations of inhibitor, from 0.0-1 mH. Net enzyme activity was measured in terms of the rate of formation of [$^3$H]benzoyl-glycine ($^3$H-hippuric acid). Under the conditions of the assay, the initial substrate concentration is approximately one-half of K$_m$. Results are expressed as I$_{50}$ values, i.e., the concentration of a given inhibitor required to reduce enzyme activity by half.

TABLE I
INHIBITION OF HUMAN URINARY ANGIOTENSIN CONVERTING ENZYME BY BPP$_{9a}$ AND ITS DERIVATIVES CONTAINING L-3,4-DEHYDROPROLINE IN PLACE OF L-PROLINE

|      | Compound            | I$_{50}$ |
|------|---------------------|----------|
|      | BPP$_{9a}$          | 28nM     |
| I.   | $\Delta$ Pro$^3$—BPP$_{9a}$ | 0.9nM    |
| II.  | $\Delta$ Pro$^5$—BPP$_{9a}$ | 0.9nM    |
| III. | $\Delta$ Pro$^8$—BPP$_{9a}$ | 60nM     |
| IV.  | $\Delta$ Pro$^9$—BPP$_{9a}$ | 0.15nM   |

Thus, $\Delta$Pro$^3$-BPP$_{9a}$ and $\Delta$Pro$^5$-BPP$_{9a}$ are approximately 30-times more active than BPP$_{9a}$, and $\Delta$Pro$^9$-BPP$_{9a}$ is 100- to 150-times more potent than BPP$_{9a}$. In view of the essential role played by angiotensin converting enzyme in renin-related hypertensive cardiovascular disease, it is evident that $\Delta$Pro$^3$-BPP$_{9a}$, $\Delta$Pro$^5$-BPP$_{9a}$, and $\Delta$Pro$^9$-BPP$_{9a}$ are likely to offer significant advantages over BPP$_{9a}$ as antihypertensive agents.

Further increases in potency may well be obtainable by inserting $\Delta$Pro in two or more positions of BPP$_{9a}$; for example, $\Delta$Pro$^{3,5}$-BPP$_{9a}$, $\Delta$Pro$^{3,9}$-BPP$_{9a}$, $\Delta$Pro$^{5,9}$-BPP$_{9a}$, $\Delta$Pro$^{3,5,9}$-BPP$_{9a}$.

It will be understood that I$_{50}$ values are directly comparable when, as in this example, all potential factors affecting the reaction rate are kept constant. These factors include the source of enzyme, its purity, the substrate used and its concentration, and the composition of the assay buffer. The data present herein are significant for the purpose of demonstrating relative inhibitory potency, but the I$_{50}$ value for BPP$_{9a}$ may differ from values reported elsewhere. For example, Cushman, et al., supra, reported an I$_{50}$ value for BPP$_{9a}$ of approximately 1000 nM, whereas Dorer, F.E., et al., *Biochim. Biophys. Acta* 429, 220 (1976) reported I$_{50}$ values in the range 12nM-15nM. The sources of such variations are not known.

EXAMPLE 3

$\Delta$Pro$^3$-BPP$_{9a}$ and $\Delta$Pro$^5$-BPP$_{9a}$ were tested for their ability to reduce mean arterial blood pressure of guinea pigs anesthetized with pentobarbital, an anesthetic thought to activate the renin-angiotensin system. Female guinea pigs (500-700 g body wgt.) of the Ft. Detrick-Hartley strain were injected intraperitoneally with pentobarbital, 30 mg/kg. Tracheostomy was performed, and the animals were ventilated with a small animal respirator. A polyethylene cannula was inserted into a femoral vein, and heparin, 1,000 units, was injected. A second cannula was inserted into a femoral artery for measurement of arterial blood pressure. The arterial cannula was connected to a pressure transducer, and the transducer was connected to a polygraph. Lead II of the electrocardiogram was monitored continuously.

Each of three guinea pigs received a single intravenous injection of $\Delta$Pro$^3$-BPP$_{9a}$, 2 mg in 0.25 ml of 0.9% (w/v) NaCl. On average, mean arterial blood pressure fell by 57.2% (81.7 mmHg to 35 mmHg). The maximum reduction was achieved within 15 sec. of injection. Each of seven guinea pigs received a single intravenous injection of $\Delta$Pro$^5$-BPP$_{9a}$, 2 mg in 0.25 ml of saline. Mean arterial blood pressure was reduced by 64.5% (78.6 to 27.9 mmHg) within 20 sec. of injection. Although the changes of blood pressure caused by $\Delta$Pro$^3$-BPP$_{9a}$ and $\Delta$Pro$^5$-BPP$_{9a}$ were large (reduction of blood pressure to levels regarded as shock levels), the test animals showed no ill effects. Except for slight increases in heart rate (0-10%), no abnormalities were observed in the electrocardiogram.

Thus, $\Delta$Pro$^3$-BPP$_{9a}$ and $\Delta$Pro$^5$-BPP$_{9a}$ are effective blood pressure reducing agents when injected intravenously into guinea pig anesthetized with pentobarbital.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

I claim:

1. A peptide comprising the amino acid sequence <Glu-Trp-A$_3$-Arg-A$_5$-Gln-Ile-A$_8$-A$_9$ wherein:
   A$_3$ is L-Proline or L-3,4-dehydroproline,
   A$_5$ is L-Proline or L-3,4-dehydroproline, $A_8$ is L-Proline or L-3,4-dehydroproline, $A_9$ is L-Proline or L-3,4-dehydroproline, at least one of $A_3$, $A_5$, $A_8$ and $A_9$ is L-3,4-dehydroproline and all amino acids are in the L configuration.

2. The peptide of claim 1 wherein $A_3$ is L-3,4-dehydroproline and $A_5$, $A_8$ and $A_9$ are L-proline.

3. The peptide of claim 1 wherein $A_5$ is L-3,4-dehydroproline and $A_3$, $A_8$ and $A_9$ are L-proline.

4. The peptide of claim 1 wherein $A_9$ is L-3,4-dehydroproline and $A_3$, $A_5$ and $A_8$ are L-proline.

5. A peptide comprising the amino acid sequence <Glu-Trp-$A_3$-Arg-$A_5$-Gln-Ile-$A_8$-$A_9$ wherein:

$A_3$ is L-Proline or L-3,4-dehydroproline, $A_5$ is L-Proline or L-3,4-dehydroproline, $A_8$ is L-Proline or L-3,4-dehydroproline, $A_9$ is L-Proline or L-3,4-dehydroproline, not more than one of $A_3$, $A_5$, $A_8$ and $A_9$ is L-3,4-dehydroproline and all amino acids are in the L-configuration.

6. A method for inhibiting angiotensin converting enzyme in vivo comprising administering an effective dose of an inhibiting peptide selected from the group consisting of peptides comprising the amino acid sequence <Glu-Trp-$A_3$-Arg-$A_5$-Gln-Ile-$A_8$-$A_9$ wherein:

$A_3$ is L-Proline or L-3,4-dehydroproline, $A_5$ is L-Proline or L-3,4-dehydroproline, $A_8$ is L-Proline or L-3,4-dehydroproline, $A_9$ is L-Proline or L-3,4-dehydroproline, at least one of $A_3$, $A_5$, $A_8$ and $A_9$ is L-3,4-dehydroproline and all amino acids are in the L-configuration.

7. The method of claim 6 wherein the inhibiting peptide is $\Delta Pro^3$-$BPP_{9a}$.

8. The method of claim 6 wherein the inhibiting peptide is $\Delta Pro^5$-$BPP_{9a}$.

9. The method of claim 6 wherein the inhibiting peptide is $\Delta Pro^9$-$BPP_{9a}$.

10. A method for inhibiting angiotensin converting enzyme in vivo comprising administering an effective dose of an inhibiting peptide selected from the group consisting of peptides comprising the amino acid sequence <Glu-Trp-$A_3$-Arg-$A_5$-Gln-Ile-$A_8$-$A_9$ wherein:

$A_3$ is L-Proline or L-3,4-dehydroproline, $A_5$ is L-Proline or L-3,4-dehydroproline, $A_8$ is L-Proline or L-3,4-dehydroproline, $A_9$ is L-Proline or L-3,4-dehydroproline, not more than one of $A_3$, $A_5$, $A_8$ and $A_9$ is L-3,4-dehydroproline and all amino acids are in the L-configuration.

11. A method for lowering blood pressure in vivo comprising administering an effective dose of a peptide selected from the group consisting of peptides having the amino acid sequence <Glu-Trp-$A_3$-Arg-$A_5$-Gln-Ile-$A_8$-$A_9$ wherein:

$A_3$ is L-Proline or L-3,4-dehydroproline, $A_5$ is L-Proline or L-3,4-dehydroproline, $A_8$ is L-Proline or L-3,4-dehydroproline, $A_9$ is L-Proline or L-3,4-dehydroproline, at least one of $A_3$, $A_5$, $A_8$ and $A_9$ is L-3,4-dehydroproline and all amino acids are in the L-configuration.

12. The method of claim 11 wherein the inhibiting peptide is $\Delta Pro^3$-$BPP_{9a}$.

13. The method of claim 11 wherein the inhibiting peptide is $\Delta Pro^5$-$BPP_{9a}$.

14. The method of claim 11 wherein the inhibiting peptide is $\Delta Pro^9$-$BPP_{9a}$.

15. A method for lowering blood pressure in vivo comprising administering an effective dose of a peptide selected from the group consisting of peptides having the amino acid sequence <Glu-Trp-$A_3$-Arg-$A_5$-Gln-Ile-$A_8$-$A_9$ wherein:

$A_3$ is L-Proline or L-3,4-dehydroproline, $A_5$ is L-Proline or L-3,4-dehydroproline, $A_8$ is L-Proline or L-3,4-dehydroproline, $A_9$ is L-Proline or L-3,4-dehydroproline, not more than one of $A_3$, $A_5$, $A_8$ and $A_9$ is L-3,4-dehydroproline and all amino acids are in the L-configuration.

* * * * *